United States Patent
Boyaci

(10) Patent No.: US 11,423,534 B2
(45) Date of Patent: Aug. 23, 2022

(54) SYSTEM AND METHOD FOR DIAGNOSING POTENTIAL DISEASES FROM PHOTO AND VIDEO DATA AND INFORMING THE USER

(71) Applicant: TURKCELL TEKNOLOJI ARASTIRMA VE GELISTIRME ANONIM SIRKETI, Istanbul (TR)

(72) Inventor: Avedis Boyaci, Istanbul (TR)

(73) Assignee: TURKCELL TEKNOLOJI ARASTIRMA VE GELISTIRME ANONIM SSIRKETI, Istanbul (TR)

( * ) Notice: Subject to any disclaimer, the term of this patent is extended or adjusted under 35 U.S.C. 154(b) by 27 days.

(21) Appl. No.: 16/771,262

(22) PCT Filed: Dec. 12, 2018

(86) PCT No.: PCT/TR2018/050796
§ 371 (c)(1),
(2) Date: Jun. 10, 2020

(87) PCT Pub. No.: WO2019/226131
PCT Pub. Date: Nov. 28, 2019

(65) Prior Publication Data
US 2021/0366105 A1 Nov. 25, 2021

(30) Foreign Application Priority Data
Dec. 12, 2017 (TR) .................................. 2017/20198

(51) Int. Cl.
| | | |
|---|---|---|
| *G06T 7/00* | (2017.01) | |
| *G16H 70/60* | (2018.01) | |
| *G16H 30/40* | (2018.01) | |
| *G06V 40/50* | (2022.01) | |

(Continued)

(52) U.S. Cl.
CPC .......... *G06T 7/0012* (2013.01); *G06V 40/161* (2022.01); *G06V 40/172* (2022.01); *G06V 40/50* (2022.01); *G16H 30/40* (2018.01); *G16H 70/60* (2018.01); *G06T 2207/10016* (2013.01);

(Continued)

(58) Field of Classification Search
CPC ....... G06T 7/0012; G16H 70/60; G16H 30/40
See application file for complete search history.

(56) References Cited

U.S. PATENT DOCUMENTS

2006/0247502 A1* 11/2006 Chen .................. G06K 9/00362
600/300
2010/0271395 A1* 10/2010 Isogai .................. G06F 16/583
345/635

(Continued)

FOREIGN PATENT DOCUMENTS

| | | |
|---|---|---|
| CN | 103690149 A | 4/2014 |
| CN | 104636580 A | 5/2015 |
| WO | 2014/031201 A2 | 2/2014 |

OTHER PUBLICATIONS

ISR for International Application PCT/TR2018/050796.

(Continued)

*Primary Examiner* — Edward Park
(74) *Attorney, Agent, or Firm* — Ladas & Parry LLP

(57) ABSTRACT

The present invention relates to a system and method for diagnosing potential diseases by making facial analysis via image processing techniques from photo and video data available in cloud storing unit and informing the user.

10 Claims, 2 Drawing Sheets

Figure 1:
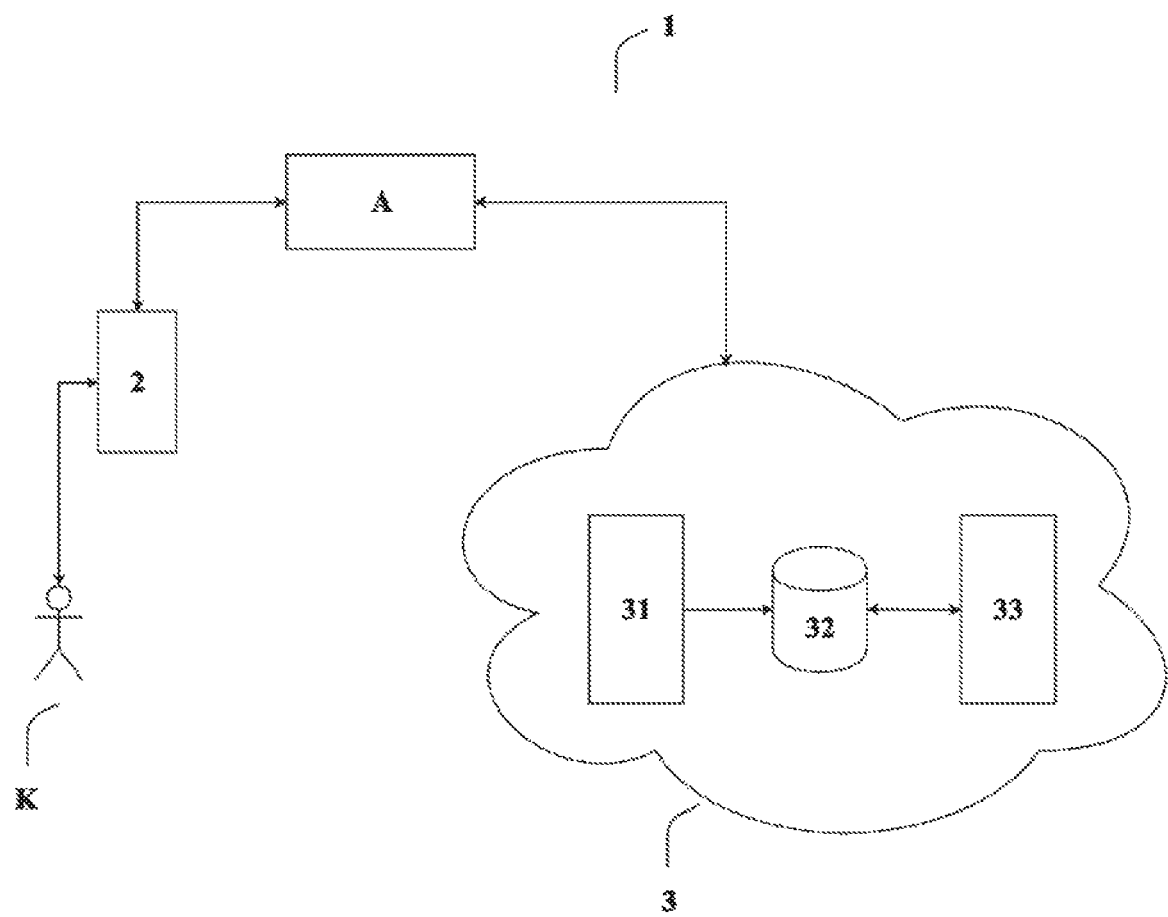

(51) Int. Cl.
　　　*G06V 40/16*　　　(2022.01)
　　　*H04L 67/1097*　　(2022.01)
(52) U.S. Cl.
　　　CPC .............. *G06T 2207/30004* (2013.01); *G06T 2207/30201* (2013.01); *H04L 67/1097* (2013.01)

(56) References Cited

U.S. PATENT DOCUMENTS

| 2015/0131872 A1* | 5/2015 | Ganong ............. G06K 9/00677 |
| | | 382/118 |
| 2016/0006941 A1* | 1/2016 | Kim ...................... G06T 7/0012 |
| | | 348/77 |
| 2017/0011192 A1 | 1/2017 | Arshad |

OTHER PUBLICATIONS

Written Opinion for International Application PCT/TR2018/050796.
CN 103690149 A_English Translation.
CN 104636580 A_English Translation.

* cited by examiner

SYSTEM AND METHOD FOR DIAGNOSING POTENTIAL DISEASES FROM PHOTO AND VIDEO DATA AND INFORMING THE USER

RELATED APPLICATION

This application is an application under 35 U.S.C. 371 of International Application No. PCT/TR2018/050796 filed on 12 Dec. 2018, which claims priority from Turkish Application No. 2017/20198 filed on 12 Dec. 2017, the disclosures of which are incorporated in their entirety by reference herein.

TECHNICAL FIELD

The present invention relates to a system and method for diagnosing potential diseases from photo and video data available in cloud storing systems and informing the user by making facial analysis via image processing techniques.

BACKGROUND OF THE INVENTION

Early diagnosis is a very important issue for protection of human health and a healthy life. Many diseases lead to some changes on appearances of human. Some of these changes occurring on appearances are understood by everybody whereas some of them can be realized only by highly experienced physicians.

With advancement of image processing methods in recent years, detailed analysis can be made in fields such as detailed face, eye, iris, pupil, skin tones, facial features and head posture in face recognition. Diseases or potential diseases can be diagnosed in persons by means of findings detected as a result of these analysis.

In the state of the art, it is specifically required to upload images to a system or to take image by means of a device finding face images in order to perform disease analysis from face images.

The Chinese patent document no. CN103690149, an application in the state of the art, discloses a mobile terminal application which diagnosis physical condition of a user by means of face recognition. The mobile terminal mentioned in the invention can be a mobile device or a device including a Wi-Fi card in it. The system uses a photo taken by a camera with a face recognition system. In addition, shooting time of the photo is not important and a photo taken at any time can be used as well. The system suggests treatment method to the user upon changes, abnormalities in different portions of the face are examined through an image recognizing technology. The invention also analyses eye and tongue characteristic. It tabularizes the health state in the form of face, eye and tongue state and stores it in its database. It analyses the physical condition of the user by comparing the stored data with the data in its database, in the processing module. The system also uses Chinese medicine. In Chinese medicine, different areas on face indicate different organs in the body. It warns the user about potential diseases with this method.

The Chinese patent document no. CN104636580, another application in the state of the art, discloses a health monitoring system based on human face. The invention warns the user by capturing and storing instant face images of the user when s/he uses the mobile device, performing facial analysis, evaluating the health status. The system consists of a mobile device user identification module, a mobile device camera control module, a human face image collecting module, a human face recognition module, a disease classification module, a health status warning module, a health status file management module, a model learning module according to face recognition module and a disease identification learning module according to face recognition module. The mobile device user identification module interprets whether the person using the mobile device is the actual user or not and then initiates the transaction of capturing face image if s/he is the actual user. As soon as it is convenient to obtain face image, the mobile device switches on the control module and transmits the obtained face images to the face image obtaining module. The face image obtaining module prepares the incoming images and sends them to the face recognition module. And the face recognition module transmits the data to the disease classification module upon controlling whether the person in the image is the actual user or not. The diagnosis occurring in the disease classification module is notified to the user by means of the health status warning module. In addition, the data are stored in the health status file management module as statistical data to be used later. New data are provided to the disease classification module upon these filed data are used by the model learning module according to the face recognition module and by the disease identification learning module according to the face recognition module.

The International patent document no. WO2014031201, another application in the state of the art, discloses a mobile technology for providing treatment by means of instant phone. The invention realizes diagnosis and patient management by using machine learning and provides medical treatment to the user by means of cloud-based data calculation and storage. The user signs up to the mobile system and sends the image of the area that s/he considers as diseased to the cloud database upon entering the necessary information. The system performs disease diagnosis learning by using machine learning when the uploaded images are being diagnosed by the connection between the user and the doctor. After machine learning verification is provided, the system gives diagnosis and treatment method by itself.

SUMMARY OF THE INVENTION

An objective of the present invention is to realize a system for diagnosing potential diseases from photo and video data available in cloud storing systems and informing the user by making facial analysis via image processing techniques and a method wherein this system is used.

DETAILED DESCRIPTION OF THE INVENTION

Figure 2:
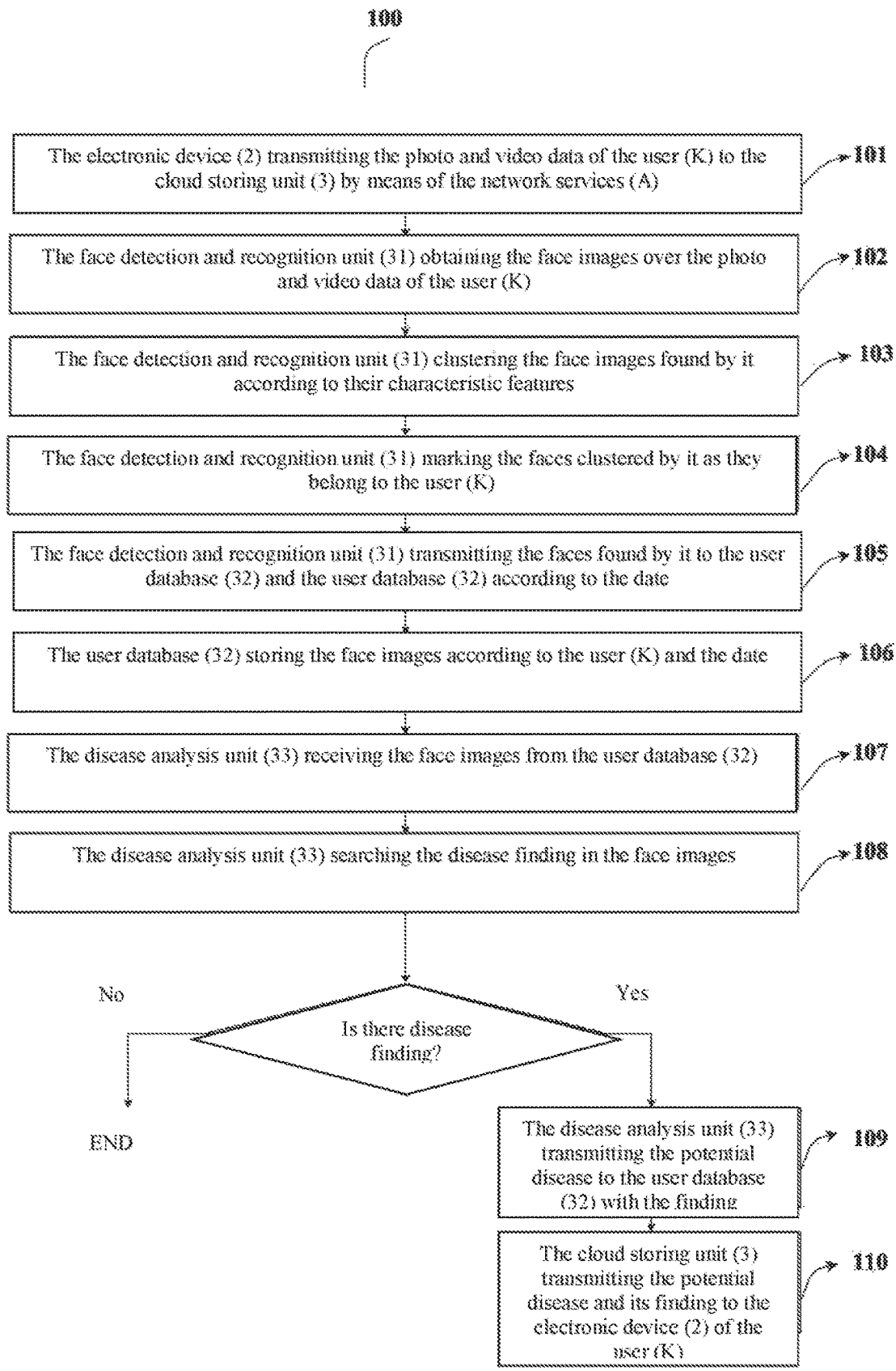

"A System and Method for Diagnosing Potential Diseases from Photo and Video Data and Informing the User" realized to fulfil the objective of the present invention is shown in the figure attached, in which:

FIG. 1 is a schematic view of the inventive system.
FIG. 2 is a flow chart of the inventive method.

The components illustrated in the figure are individually numbered, where the numbers refer to the following:
1. System
2. Electronic device
3. Cloud storing unit
    31. Face detection and recognition unit
    32. User database
    33. Disease analysis unit
K. User
A. Network services
100. Method The inventive system (1) for diagnosing potential diseases from photo and video data comprises:
- at least one electronic device (2) whereby the users (K) can upload their photo and video data
- at least one cloud storing unit (3) whereby the electronic devices (2) can transmit the photo and video data by means of the network services (A) and receive feedback;
- at least one face detection and recognition unit (31) which is included within the cloud storing unit (3) and which finds the face in the photo and video data and detects whose faces are these;
- at least one user database (32) which is included within the cloud storing unit (3) and keeps the analysed faces as date and name;
- at least one disease analysis unit (33) which is included within the cloud storing unit (3) and detects the disease by analysing the faces included in the user database (32).

The electronic device (2) is a device whereby the users (K) can upload their photo and video data and which transmits the image data uploaded by means of the network services (A), to the cloud storing unit (3). In a preferred embodiment of the invention, the electronic device (2) is a computer or a mobile device.

The cloud storing unit (3) is a remote storage unit whereby the electronic devices (2) can upload the photo and video data of the users (K) by means of the network services (A). The cloud storing unit (3) comprises the face detection and recognition unit (31), the user database (32) and the disease analysis unit (33).

The face detection and recognition unit (31) is a unit which detects face images via image processing techniques from the photo and video data uploaded to the cloud storing unit (3), clusters the similar faces found by it by combining the characteristic features of the face and marks the clustered faces as they belong to one person.

The user database (32) is a database which stores the faces clustered by the face detection and recognition unit (31) by their user (K) names and dates.

The disease analysis unit (33) is a unit which keeps the characteristic features that can be detected in face images for different diseases, as disease findings. The disease analysis unit (33) detects the findings of diseases in face images by analysing the images received from the user database (32), via image processing techniques.

In one embodiment of the invention, the disease analysis unit (33) diagnoses diseases by analysis of sequential face image. It keeps the changes or the abnormalities in the face images of different dates that it receives from the user database (32), as finding coefficients. Disease is diagnosed when courses are detected more than a specific finding coefficient.

S In one embodiment of the invention, the user database (32) keeps the disease and the findings of the disease with the user (K) names in the event that a disease is diagnosed in the face images of the user (K) by the disease analysis unit (33).

The cloud storing unit (3) sends the disease findings detected by the disease analysis unit (33) and stored in the user database (32), to the electronic device (2) of the user (K). The cloud storing unit (3) transmits the disease and the disease findings to an electronic device (2) of the user (K) by means of the network services (A) as e-mail, sms or push notification.

In one embodiment of the invention, the cloud storing unit (3) transmits the changes in the face images according to the dates kept in the user database (32) and the possible reasons of these changes to the electronic devices (2) of the users (K).

The inventive method (100) for diagnosing potential diseases from photo and video data comprises steps of:
- the electronic device (2) transmitting the photo and video data of the user (K) to the cloud storing unit (3) by means of the network services (A)(101);
- the face detection and recognition unit (31) obtaining the face images over the photo and video data of the user (K)(102);
- the face detection and recognition unit (31) clustering the face images found by it according to their characteristic features (103);
- the face detection and recognition unit (31) marking the faces clustered by it as they belong to the user (K)(104);
- the face detection and recognition unit (31) transmitting the faces found by it to the user database (32) and the user database (32) according to the date (105);
- the user database (32) storing the face images according to the user (K) and the date (106);
- the disease analysis unit (33) receiving the face images from the user database (32)(107);
- the disease analysis unit (33) searching the disease finding in the face images (108);
- the disease analysis unit (33) transmitting the potential disease to the user database (32) with the finding if it detects a disease finding (109);
- if the disease finding of the user (K) is added to the user database (32), the cloud storing unit (3) transmitting the potential disease and its finding to the electronic device (2) of the user (K) (110).

Within these basic concepts; it is possible to develop various embodiments of the inventive system (1) and method (100); the invention cannot be limited to examples disclosed herein and it is essentially according to claims.

The invention claimed is:

1. A system for diagnosing potential diseases from photo and video data and informing a user; comprising:
   at least one electronic device to where at least one user can upload photo and video data;
   at least one cloud storing unit whereby the at least one electronic device can transmit the photo and video data by means of network services and receive feedback; the at least one cloud storing unit having a processor and a memory configured to store processor-executable instructions, wherein when the processor-executable instructions are executed, the processor is configured to:
   receive and store the photo and video data;
   find a face in the photo and video data and detect which user the face belongs to by detecting face images from the photo and video data using image processing techniques, clustering similar faces detected by combining characteristic features of the faces, and marking the clustered faces belonging to one user;
   store the detected and marked face images by date and name;
   detect a potential disease by analyzing the stored face images using image processing techniques and storing changes or abnormalities detected in the stored face images of different dates as finding coefficients and detecting a potential disease when courses detected are greater than a specific finding coefficient.

2. The system according to claim 1; wherein the processor is further configured to store in a user database the characteristic features that can be detected in face images for different diseases, as disease findings.

3. The system according to claim 2; wherein processor is further configured to store in the user database the disease and the findings of the disease with the user names in the event that a disease is diagnosed in the face images of the user.

4. The system according to claim 1; wherein processor is further configured to send the disease findings detected and stored in a user database, to the electronic device of the user.

5. The system according to claim 4; wherein the processor is further configured to transmit the disease and the disease findings to the electronic device of the user by means of the network services as e-mail, sms or push notification.

6. The system according to claim 4; wherein the processor is further configured to transmit the changes in the face images according to the dates kept in the user database (32) and the possible reasons of these changes to the electronic devices of the user.

7. The system according to claim 1, wherein the processor is further configured to detect a potential disease by analyzing the stored face images sequentially.

8. A method (100) for diagnosing potential diseases from photo and video data and informing a user; comprising:
  transmitting by an electronic device the photo and video data of the user to a cloud storing unit by means of network services;
  finding by a face detection and recognition unit a face in the photo and video data and detecting which user the face belongs to by detecting face images from the photo and video data of the user, clustering similar faces detected according to their characteristic features, marking the clustered faces belonging to one user, and transmitting the detected and marked face images to a user database,
  storing in the user database the detected and marked face images according to user name and date;
  receiving in a disease analysis unit the face images from the user database, searching for a potential disease finding in the face images, detecting a potential disease by analyzing the face images using image processing techniques and storing changes or abnormalities detected in the face images of different dates as finding coefficients, detecting a potential disease when courses detected are greater than a specific finding coefficient, and transmitting the potential disease to the user database with the potential disease finding if a potential disease finding is detected; and
  if the potential disease finding of the user is added to the user database, transmitting by the cloud storing unit the potential disease finding to the electronic device of the user.

9. A system for diagnosing potential diseases from photo and video data and informing a user; comprising:
  at least one electronic device (2) to where at least one user (K) can upload the user's photo and video data;
  at least one cloud storing unit (3) whereby the at least one electronic device (2) can transmit the photo and video data by means of network services (A) and receive feedback; the at least one cloud storing unit (3) having a
  a processor and a memory configured to store processor-executable instructions, wherein when the processor-executable instructions are executed, the processor is configured to:
  receive and store the photo and video data;
  find a face in the photo and video data and detect which user the face belongs to by detecting face images from the photo and video data using image processing techniques, clustering similar faces detected by combining characteristic features of the faces, and marking the clustered faces belonging to one user;
  store the detected and marked face images by date and name;
  detect a potential disease by analyzing the stored face images using image processing techniques and storing changes or abnormalities detected in the stored face images of different dates as finding coefficients and detecting a potential disease when courses detected are greater than a specific finding coefficient.

10. The system according to claim 9, wherein the processor is further configured to detect a potential disease by analyzing the stored face images sequentially.

* * * * *